US012708657B2

(12) United States Patent
Kim et al.

(10) Patent No.: US 12,708,657 B2
(45) Date of Patent: Aug. 18, 2026

(54) PHARMACEUTICAL COMPOSITION FOR TREATING DEGENERATIVE BRAIN DISEASE, INCLUDING GLYCINE TRANSPORTER AS ACTIVE INGREDIENT

(71) Applicant: AMYLOID SOLUTION INC., Seongnam-si (KR)

(72) Inventors: Seong Muk Kim, Seoul (KR); Seongjeong Park, Yongin-si (KR); Hye-ju Kim, Hwaseong-si (KR); Youngsoo Kim, Incheon (KR); Hyeyun Kim, Incheon (KR)

(73) Assignee: AMYLOID SOLUTION INC., Seongnam-si (KR)

( * ) Notice: Subject to any disclaimer, the term of this patent is extended or adjusted under 35 U.S.C. 154(b) by 815 days.

(21) Appl. No.: 18/046,296

(22) Filed: Oct. 13, 2022

(65) Prior Publication Data

US 2023/0190872 A1 Jun. 22, 2023

Related U.S. Application Data

(63) Continuation-in-part of application No. PCT/KR2021/003520, filed on Mar. 22, 2021.

(30) Foreign Application Priority Data

Apr. 14, 2020 (KR) ........................ 10-2020-0044988
Mar. 10, 2021 (KR) ........................ 10-2021-0031435

(51) Int. Cl.
*A61K 38/17* (2006.01)
*A61P 25/28* (2006.01)
*C12N 15/86* (2006.01)

(52) U.S. Cl.
CPC .......... *A61K 38/1709* (2013.01); *A61P 25/28* (2018.01); *C12N 15/86* (2013.01)

(58) Field of Classification Search
CPC .............. A61K 38/1709; A61K 35/761; A61K 48/005; A61K 48/0075; A61P 25/28; C12N 15/86; C12N 2750/14143; A01K 67/0275; A01K 2217/052; A01K 2217/15; A01K 2227/105; A01K 2267/0312; C07K 14/47
See application file for complete search history.

(56) References Cited

U.S. PATENT DOCUMENTS

| | | | |
|---|---|---|---|
| 5,824,486 | A | 10/1998 | Borden et al. |
| 6,008,015 | A | 12/1999 | Albert et al. |
| 6,238,883 | B1 | 5/2001 | Brown et al. |
| 6,251,617 | B1 | 6/2001 | Albert et al. |

FOREIGN PATENT DOCUMENTS

| | | | |
|---|---|---|---|
| JP | 2001-521388 | A | 11/2001 |
| JP | 2002-514882 | A | 5/2002 |
| JP | 2010-517964 | A | 5/2010 |
| JP | 2015-157764 | A | 9/2015 |
| WO | 93/10228 | A1 | 5/1993 |
| WO | 00/29564 | A2 | 5/2000 |

OTHER PUBLICATIONS

Jean C. Augustinack, et al., "Specific tau phosphorylation sites correlate with severity of neuronal cytopathology in Alzheimer's disease", Acta Neuropathol, 2002, pp. 26-35, vol. 103.
International Search Report for PCT/KR2021/003520 dated Jul. 1, 2021 [PCT/ISA/210].
"*Homo sapiens* solute carrier family 6 member 9 (SLC6A9), transcript variant 1, mRNA"; NCBI Reference Sequence: NM_006934.4; National Library of Medicine, National Center for Biotechnology Information (NIH); 2016 (4 pages).
Nouri Nayerossadat et al; "Viral and nonviral delivery systems for gene delivery"; Advanced Biomedical Research; Apr.-Jun. 2012; vol. 1; Issue 2; pp. 1-11.
Eloise Hudry et al.; "Therapeutic AAV Gene Transfer to the Nervous System: A Clinical Reality"; Neuron 101, Mar. 6, 2019; Published by Elsevier Inc.; pp. 839-862; Neuron, vol. 102, Issue 1, Apr. 3, 2019; pp. 263 (Correction).

*Primary Examiner* — Olga N Chernyshev
(74) *Attorney, Agent, or Firm* — Sughrue Mion, PLLC

(57) ABSTRACT

Provided is a pharmaceutical composition for treating a degenerative brain disease, including a glycine transporter as an active ingredient. A composition including, as an active ingredient, a glycine transporter protein, a fragment thereof or a nucleic acid molecule encoding the protein or the fragment thereof, a vector including the nucleic acid molecule, or a cell transformed with the vector including the nucleic acid molecule, according to an embodiment, not only can achieve excellent effect(s) of inhibiting amyloid-beta aggregation and/or degrading aggregated amyloid-beta, but also degrades tau protein (and/or inhibition of the aggregation thereof), inhibits the hyperphosphorylation of tau protein, and has excellent blood-brain barrier permeability, thus making it possible to successively act on brain tissues. Therefore, the composition can be effectively applied to the prevention and/or treatment of various degenerative brain diseases associated with amyloid-beta aggregation, tau protein aggregation, and/or hyperphosphorylated tau protein.

5 Claims, 3 Drawing Sheets

Specification includes a Sequence Listing.

Fig. 4
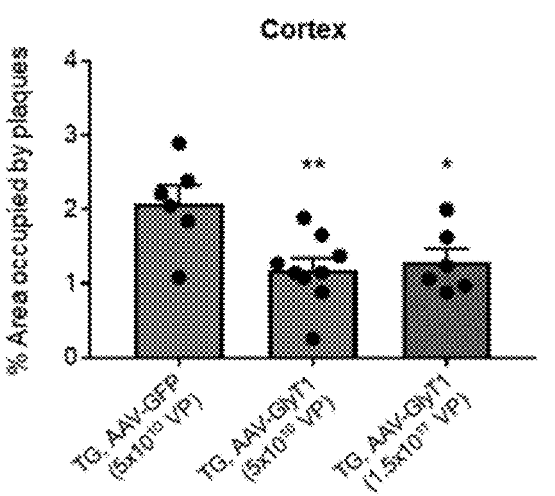
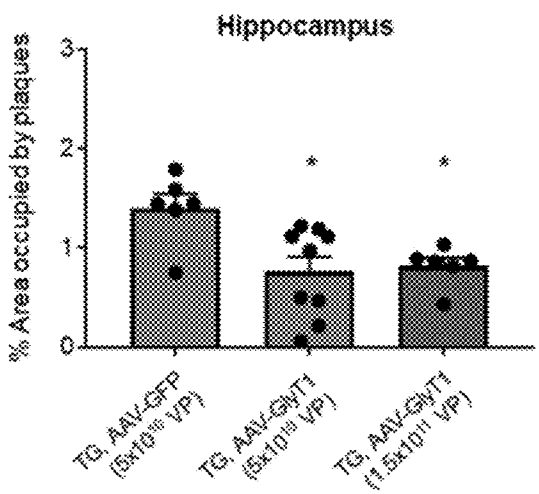
Fig. 5
Spontaneous Alternation (%)
80
60
40
20
0
**
*
**
WT, Veh
TG, AAV-GFP (5x10$^{10}$ VP)
TG, AAV-GlyT1 (5x10$^{10}$ VP)
TG, AAV-GlyT1 (1.5x10$^{11}$ VP)

PHARMACEUTICAL COMPOSITION FOR TREATING DEGENERATIVE BRAIN DISEASE, INCLUDING GLYCINE TRANSPORTER AS ACTIVE INGREDIENT

CROSS-REFERENCE TO RELATED APPLICATIONS

This application is a bypass continuation-in-part of PCT International Application No. PCT/KR2021/003520 filed on Mar. 22, 2021, which is based on and claims priority to Korean Patent Application No. 10-2020-0044988 filed on Apr. 14, 2020 and Korean Patent Application No. 10-2021-0031435 filed on Mar. 10, 2021, the disclosures of which are incorporated herein by reference in their entireties.

INCORPORATION BY REFERENCE OF SEQUENCE LISTING

The content of the electronically submitted sequence listing, file name: Q280637_Sequence_Listing_As_Filed.XML; size: 3,732 bytes; and date of creation: Oct. 13, 2022, filed herewith, is incorporated herein by reference in their entirety.

TECHNICAL FIELD

The present disclosure relates to a pharmaceutical composition for treating a degenerative brain disease, including a glycine transporter as an active ingredient.

BACKGROUND ART

Degenerative brain diseases are diseases that cause degenerative changes in nerve cells of the central nervous system and thus leads to various symptoms such as impaired motor and sensory functions, and inhibition of higher-order causative functions such as memory, learning, and arithmetic reasoning. Common degenerative brain diseases include Alzheimer's disease, Parkinson's disease, memory disorders, and the like. In degenerative brain diseases, neuronal cell death occurs due to rapid or slow progression of necrosis or apoptosis. Therefore, for the development of a method of preventing, regulating, and treating central nervous system diseases, the mechanism of death of neurons needs to be understood.

Meanwhile, an important pathological feature of Alzheimer's disease, which is a degenerative brain disease, is the formation of peptide aggregates called senile plaques, which cause synaptic dysfunction and neuronal death. The main component of these senile plaques is amyloid-beta having a length of 40-42 amino acids. Amyloid-beta monomers easily self-assemble into oligomers, protofibrils, and beta-sheet-rich fibrils, and are associated with the development of neurotoxicity.

The correlation between amyloid-beta plaques and neurotoxicity has not yet been identified. However, the self-assembly of amyloid-beta into intermediate oligomers or aggregates is considered to be associated with the development of neurological diseases such as Alzheimer's disease.

Therefore, the inventors of the present disclosure completed the present disclosure relating to the treatment of degenerative brain diseases through inhibition of the formation of amyloid-beta plaques.

DESCRIPTION OF EMBODIMENTS

Technical Problem

One aspect provides a method of preventing, ameliorating or treating degenerative brain disease, the method comprising of increasing the expression or activity of glycine transporter protein in a subject with degenerative brain disease.

Another aspect provides a pharmaceutical composition for the prevention or treatment of a degenerative brain disease, including a glycine transporter protein, a fragment thereof, or a nucleic acid molecule encoding the protein or the fragment thereof, as an active ingredient.

Another aspect provides a pharmaceutical composition for the prevention or treatment of a degenerative brain disease, including a vector including a nucleic acid molecule encoding a glycine transporter protein or a fragment thereof, as an active ingredient.

Another aspect provides a pharmaceutical composition for the prevention or treatment of a degenerative brain disease, including a cell transformed with a vector including a nucleic acid molecule encoding a glycine transporter protein or a fragment thereof, as an active ingredient.

Another aspect provides a method of preventing or treating a degenerative brain disease, including administering, to a subject in need thereof, a glycine transporter protein, a fragment thereof, or a nucleic acid molecule encoding the protein or the fragment thereof.

Another aspect provides use of a glycine transporter protein, a fragment thereof, or a nucleic acid molecule encoding the protein or the fragment thereof for the preparation of a composition for preventing or treating a degenerative brain disease.

Technical Solution to Problem

One aspect provides a method of preventing, ameliorating or treating degenerative brain disease, the method comprising of increasing the expression or activity of glycine transporter protein in a subject with degenerative brain disease.

In an embodiment, the increasing the expression or activity of glycine transporter protein comprises administering to the subject therapeutically effective amount of a glycine transporter protein, a fragment thereof, or a nucleic acid molecule encoding the protein or the fragment thereof.

Another aspect provides a pharmaceutical composition for the prevention or treatment of a degenerative brain disease, including a glycine transporter protein, a fragment thereof, or a nucleic acid molecule encoding the protein or the fragment thereof, as an active ingredient.

The glycine transporter is a neurotransmitter transporter, and may terminate glycine signal transduction by reabsorbing glycine from the synaptic cleft back to the presynaptic neuron. Accordingly, in an embodiment, a glycine receptor may promote intracellular transport of extracellular glycine.

In an embodiment, the glycine transporter may be glycine transporter-1 (GlyT1), and the GlyT1 may include the polynucleotide sequence of SEQ ID NO: 1.

The term "polynucleotide" as used herein refers to a single-stranded or double-stranded polymer of deoxyribonucleotides or ribonucleotides. The polynucleotide may include an RNA genome sequence, DNA (gDNA and cDNA), and RNA sequences transcribed therefrom, and unless defined otherwise, may include an analog of a natural polynucleotide.

The polynucleotide may include not only a nucleotide sequence encoding the amino acid sequence of the glycine transporter protein, but also a sequence complementary to the nucleotide sequence. The complementary sequence may include not only perfectly complementary sequences, but also substantially complementary sequences. Under the stringent conditions known in the art, the complementary sequence may refer to, for example, a sequence capable of hybridizing with a nucleotide sequence of the nucleotide sequence encoding the amino acid sequence of the protein.

In an embodiment, the pharmaceutical composition may be administered to:

(1) subjects who have a higher level or a higher risk of aggregation of amyloid-beta than normal individuals not having a degenerative brain disease;
(2) subjects who have a higher level or a higher risk of aggregation of tau protein than normal individuals not having a degenerative brain disease;
(3) subjects who have a higher level or a higher risk of phosphorylation of tau protein than normal individuals not having a degenerative brain disease; and
(4) subjects corresponding to at least one of (1) to (3).

The aggregation level of the amyloid-beta or tau protein may refer to the amount (concentration) of amyloid-beta aggregates or tau protein aggregates, or a ratio of the amyloid-beta aggregate or the tau protein aggregate to the total amyloid-beta or the total tau protein.

The phosphorylation level of the tau protein may refer to the amount (concentration) of phosphorylated tau protein or the ratio of phosphorylated tau protein to the total tau protein.

Human amyloid-beta is a peptide molecule containing about 36-43 amino acids, is a major component of amyloid plaques expressed in the brain of patients with Alzheimer's disease, and is known to be involved in the development of Alzheimer's disease. The amyloid-beta peptide molecule may be obtained by cleaving an amyloid precursor protein (APP) (UniProtKB P05067) with beta secretase and gamma secretase. Amyloid-beta peptide molecules aggregate to form neuronal toxic oligomers, leading to a degenerative brain disease.

The tau protein consists of four parts including the N-terminal overhang, the proline aggregation domain, the microorganelle-binding domain, and the C-terminus (Mandelkow et al., Acta. Neuropathol., 103, 26-35, 1996). Abnormal hyperphosphorylation or modification of Tau in neurons of the central nervous system is known to cause degenerative brain diseases such as Parkinson's disease and tauopathy.

In an embodiment, the aggregation of amyloid-beta may be caused by glycine. Accordingly, the glycine transporter may inhibit the aggregation of amyloid-beta.

The term "degenerative brain disease" as used herein refers to any disease that is associated with degenerative changes in the brain, and in particular, is used to comprehensively include all diseases (brain diseases) that can be caused by factors such as the aggregation of amyloid-beta in the brain and/or brain nerve cells. In an embodiment, the degenerative brain disease may be selected from the group consisting of preclinical alzheimer's disease, dementia, Alzheimer's disease, Parkinson's disease, Huntington's disease, mild cognitive impairment, cerebral amyloid angiopathy, down syndrome, amyloid stroke, systemic amyloidosis, Dutch type amyloidosis, Niemann-Pick disease, senile dementia, amyotrophic lateral sclerosis, spinocerebellar atrophy, Tourette's syndrome, Friedrich's ataxia, Machado-Joseph's disease, Lewy body dementia, dystonia, progressive supranuclear palsy, and frontotemporal dementia, but is not limited thereto. The degenerative brain disease may include any disease that is caused by the aggregation of amyloid-beta.

The term "normal" as used herein refers to a subject not having the above-defined "degenerative brain disease" among individuals to which the pharmaceutical composition is applied and individuals of the same species, or a brain tissue or cell (brain neurons) separated and/or cultured from the individuals.

Another embodiment provides an adeno-associated virus (AAV) vector including a nucleotide sequence encoding a glycine transporter protein or a fragment thereof.

The nucleotide sequence encoding a glycine transporter or a fragment thereof may include, for example, a nucleotide sequence having at least 70%, 80%, 90%, 95%, 96%, 97%, 98%, 99%, or 100% identity with SEQ ID NO: 1, in which a protein encoded by the nucleotide sequence may substantially retain the functional activity of a protein represented by SEQ ID NO: 1.

Another embodiment provides a cell transformed with the AAV vector.

Another aspect provides a pharmaceutical composition for the prevention or treatment of a degenerative brain disease, including, as an active ingredient, a vector including a nucleic acid molecule encoding a glycine transporter protein or a fragment thereof.

In an embodiment, the vector may be any one selected from the group consisting of a plasmid vector, a cosmid vector, a bacteriophage vector, an adenoviral vector, a retroviral vector, and an adeno-associated viral vector, but is not limited thereto. In addition, the adeno-associated viral vector may be any one selected from the group consisting of AAV1, AAV2, AAV3, AAV4, AAV5, AAV6, AAV7, AAV8, AAV9, AAV10, and AAV11, but is not limited thereto.

Specifically, the present disclosure may provide an AAV vector including a nucleotide sequence encoding a glycine transporter or a fragment thereof. Preferably, the AAV vector is in the form of AAV particles. Methods of preparing and modifying a viral vector and a viral vector particle, e.g., those derived from AAV, are well known in the art.

The AAV vector may include an AAV genome or a fragment or derivative thereof. The AAV genome is a polynucleotide sequence which encodes the functions needed for the production of an AAV particle. These functions include those operating in the replication and packaging cycle for AAV in a host cell, including encapsulation of the AAV genome into an AAV particle. A naturally occurring AAV is replication-deficient and relies on the provision of helper functions in trans for completion of a replication and packaging cycle. The AAV genome may be in single-stranded form, either positive or negative-sense, or alternatively in double-stranded form. The use of a double-stranded form allows the bypass of a DNA replication step in a target cell, and thus can accelerate transgene expression.

The AAV genome may be from any naturally derived serotype, isolate or clade of AAV. Thus, the AAV genome may be the full genome of a naturally occurring AAV. As is known in the art, AAVs occurring in nature may be classified according to various biological systems. In general, AAVs are referred to in terms of serotype thereof. A serotype corresponds to a variant subspecies of AAV, which, owing to a profile of the expression of capsid surface antigens, has distinctive reactivity that can be used to distinguish same from other variant subspecies. Typically, a virus having a particular AAV serotype does not efficiently cross-react with neutralizing antibodies specific for any other AAV serotype.

AAV serotypes include AAV1, AAV2, AAV3, AAV4, AAV5, AAV6, AAV7, AAV8, AAV9, AAV10, and AAV11, and also include recombinant serotypes, such as Rec2 and Rec3, recently identified in the brain of primates. Any of these AAV serotypes may be used in the present disclosure.

AAV may also be referred to in terms of clades or clones. The AAV refers to the phylogenetic relationship of naturally derived AAVs, and typically refers to a phylogenetic group of AAVs that can be traced back to a common ancestor and includes all descendants thereof. Additionally, the AAV may be referred to in terms of a specific isolate, i.e., a genetic isolate of a specific AAV found in nature. The term genetic isolate describes a population of AAVs that have undergone limited genetic mixing with other naturally occurring AAVs, thereby defining a recognizably distinct population at a genetic level.

Those skilled in the art can select an appropriate serotype, clade, clone, or isolate of AAV for use in the present disclosure on the basis of their common general knowledge.

The adeno-associated viral (AAV) vector is constructed by introducing materials capable of producing a virus in a specific cell, and the expression vector including the nucleic acid according to the present disclosure may be introduced into a cell by methods known in the art, for example, transient transfection, microinjection, transduction, cell fusion, calcium phosphate precipitation, liposome-mediated transfection, DEAE dextran-mediated transfection, polybrene-mediated transfection, electroporation, gene gun, and other known methods of introducing nucleic acids into cells, without limitation thereto. For example, after an expression vector is constructed by inserting a glycine transporter into AAV, the vector is transduced into packaging cells, which are then cultured and filtered to obtain an AAV solution. Then, a glycine transporter gene may be introduced into cells by infecting cells, such as brain cells, neurons, and/or neural progenitors, by using the AAV solution.

The vector including AAV may refer to a means for expressing a target gene in a host cell. The vector includes elements for the expression of a target gene, and may include a replication origin, a promoter, an operator, a transcription terminator, and the like, and may further include an appropriate enzymatic site (e.g., a restriction enzyme site) for introduction into the genome of a host cell and/or a selective marker for determining successful introduction into a host cell and/or a ribosome binding site (RBS) for translation into proteins, an internal ribosome entry site (IRES), and the like. The vector may further include a transcriptional regulation sequence (e.g., an enhancer and the like) other than the promoter.

In the recombinant vector, the polynucleotide sequence encoding the protein may be operatively linked to a promoter. The term "operatively linked" refers to a functional linkage between a nucleotide expression regulatory sequence, such as a promoter sequence, and another nucleotide sequence, in which the regulatory sequence regulates the transcription and/or translation of the other nucleotide sequence.

The recombinant vector may be an expression vector capable of stably expressing the glycine transporter protein in a host cell. For the expression vector, an expression vector commonly used in the expression of a foreign protein in plants, animals, or microorganisms may be used. The recombinant vector may be constructed through various methods known in the art.

In addition, the vector may refer to an expression vector for gene therapy. Accordingly, the viral vector may refer to a viral vector capable of delivering a therapeutic gene or genetic material to a desired cell, tissue, and/or organ. The term "gene therapy" may refer to a method of normalizing functions by inserting a normal gene into a cell having genetic abnormality or providing a new function, so as to treat various genetic diseases caused by genetic abnormality. Accordingly, the recombinant vector or recombinant cell of the present disclosure can prevent or treat a degenerative brain disease by expressing the glycine transporter gene.

Another aspect provides a pharmaceutical composition for the prevention or treatment of a degenerative brain disease, including, as an active ingredient, a cell transformed with a vector including a nucleic acid molecule encoding a glycine transporter protein or a fragment thereof.

The term "transformation" as used herein refers to a change in the genetic properties of an organism by DNA given from the outside, and that is, may refer to a phenomenon in which a genetic trait changes when DNA, which is a type of nucleic acid extracted from a cell of a certain lineage of an organism, is introduced into a living cell of another lineage and enters the cell.

In an embodiment, the transformed cell may be a stem cell, a progenitor cell, or an animal cell, but s not limited thereto. In addition, the stem cell may specifically be an embryonic stem cell, an adult stem cell, or an induced pluripotent stem cell (iPS), but is not limited thereto. The stem cell may include stem cells differentiated from the stem cells, e.g., all of a mesenchymal stem cell derived from an embryonic stem cell, a mesenchymal stem cell derived from an iPS, a neural stem cell derived from an iPS, and the like. In addition, the cell may be autologous or heterologous, or allogeneic or xenogenic.

The term "treatment" as used herein is used as a meaning that comprehensively includes alleviation or amelioration of pathological symptoms, reduction of a site of a disease, delay or alleviation of disease progression, amelioration, alleviation, or stabilization of a disease state or symptoms, partial or complete recovery, prolongation of survival, other beneficial treatment outcomes, and the like. The term "prevention" is used as a meaning that includes all mechanisms and/or effects that act on a subject not having a particular disease to prevent the particular disease from developing, to delay the onset of the disease, or to reduce the frequency of the disease.

The term "pharmaceutical composition" may refer to a molecule or compound that imparts some beneficial effects upon administration to a subject. Advantageous effects include: enabling diagnostic decisions; ameliorating a disease, symptom, disorder, or condition; reducing or preventing the onset of a disease, symptom, disorder, or condition; and generally, responding to a disease, symptom, disorder, or condition.

The pharmaceutical composition may further include, in addition to the active ingredient, at least one adjuvant selected from the group consisting of a pharmaceutically acceptable carrier, an excipient, a diluent, a filler, an extender, a wetting agent, a disintegrant, an emulsifier (a surfactant), a lubricant, a sweetener, a flavoring agent, a suspending agent, a preservative, and the like. The adjuvant may be appropriately adjusted depending on the dosage form to which the pharmaceutical composition is applied, and may be one or more selected from all adjuvants that can be commonly used in the pharmaceutical field. In an embodiment, the pharmaceutically acceptable carrier may be one selected from saline, sterile water, Ringer's solution, buffered saline, dextrose solution, maltodextrin solution, glycerol, ethanol, and liposomes, and a mixture of two or more of these components, all of which are commonly used for the formulation of drugs. As needed, other conventional additives, such as an antioxidant, a buffer, and a bacteriostat, may be added. In addition, by additionally adding a diluent, a dispersant, a surfactant, a binder, and a lubricant, the pharmaceutical composition may be formulated into an injectable formulation, such as an aqueous solution, a suspension, and an emulsion, a pill, a capsule, a granule, or a tablet. In addition, to specifically act on a target organ, a target organ-specific antibody or other ligands may be combined with the carrier. Furthermore, by using an appropriate method in the art or a method disclosed in Remington's document (e.g., Remington's Pharmaceutical Science (latest edition), Mack Publishing Company, Easton Pa.), the pharmaceutical composition may be preferably formulated depending on respective diseases or components.

An effective amount of the active ingredient or the pharmaceutical composition may be administered orally or parenterally during clinical administration, and may be used in the form of a general pharmaceutical formulation. Parenteral administration may refer to administration through an administration route, such as a rectal, intravenous, peritoneal, muscle, arterial, transdermal, nasal, inhale, ocular, or subcutaneous administration route, other than oral administration, and may include topical administration to a lesion site, and the like. For oral administration, the active ingredient in the pharmaceutical composition may be coated to prevent from decomposing in the stomach, or the pharmaceutical composition may be formulated into a dosage form that is protectable from decomposition. When the pharmaceutical composition of the present disclosure is used as a medicine, at least one active ingredient that exhibits the same or similar functions may be further included.

In addition, the term "active ingredient" as used herein may refer to a physiologically active substance that is a substance mentioned herein used to achieve the aforementioned pharmacological activity (e.g., treatment of degenerative brain disease), and is distinguished from the substance mentioned herein administered alone, administered in combination with other substances, or additionally administered. That is, the glycine transporter protein, a fragment thereof or a nucleic acid molecule encoding the protein and the fragment thereof, a vector including the nucleic acid molecule, and a cell transformed with the vector including the nucleic acid molecule may be administered as a single active ingredient for a direct therapeutic effect on a degenerative brain disease.

The pharmaceutical composition may be in the form of a solution, a suspension, a syrup or an emulsion in an aqueous or oily medium, or may be formulated in the form of powder, a granule, a tablet, a capsule, or the like. For formulation, a dispersant or a stabilizer may be further included. When formulating the pharmaceutical composition, a diluent or an excipient, such as a filler, an extender, a binder, a wetting agent, a disintegrant, and a surfactant that are commonly used may be used. Formulations for the parenteral administration, a sterile aqueous solution, a non-aqueous solution, a suspension, an emulsion, a lyophilized formulation, and a suppository may be included. As a non-aqueous solvent and a suspension solvent, propylene glycol, polyethylene glycol, vegetable oil such as olive oil, an injectable ester such as ethyl oleate, and the like may be used. As a base agent for the suppository, witepsol, macrogol, tween 61, cacao butter, laurin butter, glycerol, gelatin, or the like may be used.

The pharmaceutical composition may be used by mixing with various pharmaceutically acceptable carriers, such as physiological saline or an organic solvent. To increase stability or absorptiveness of the pharmaceutical composition, carbohydrates, such as glucose, sucrose or dextran, antioxidants, such as ascorbic acid or glutathione, chelating agents, low-molecular proteins, or other stabilizers may be used as pharmaceuticals.

The pharmaceutical composition may be administered in a pharmaceutically effective amount. An administration dosage is not particularly limited, but may vary depending on absorption into the body, body weight, age, gender, and health condition of a patient, diet, administration time, administration method, excretion rate, the severity of a disease, and the like. The pharmaceutical composition of the present disclosure is prepared in consideration of the effective amount range. A unit dosage form formulated thereby may be administered using a specialized dosing method according to the judgment of an expert who monitors or observes the drug administration or a personal demand as necessary, or may be administered several times at regular time intervals. A dose of the pharmaceutical composition may be in a range of 1 μg/kg/day to 1,000 mg/kg/day, but is not limited thereto. A daily or single dose may be formulated as one formulation in a unit dose form, formulated in an appropriate amount, or prepared by internalizing in a multidose container.

The subject may be a mammal, for example, a human, a cow, a horse, a pig, a dog, sheep, a goat, or a cat. The subject may be an individual in need of treatment of degenerative brain disease.

When the active ingredient of the present disclosure is a recombinant vector, an effective amount may be in a range of 0.01 mg to 500 mg, and more specifically, 0.1 mg to 300 mg. In the case of a recombinant virus including the recombinant vector, an effective amount may be specifically in a range of $10^3$ IU to $10^{12}$ IU (10 PFU to $10^{10}$ PFU), and more specifically, $10^5$ IU to $10^{10}$ IU, but is not limited thereto.

When the active ingredient of the present disclosure is a cell, an effective amount may be in a range of $10^3$ cells to $10^8$ cells, and more specifically, $10^4$ cells to $10^7$ cells, but is not limited thereto.

The effective dose of the composition of the present disclosure may be, per 1 kg of the body weight, in a range of 0.05 mg/kg to 12.5 mg/kg in the case of the recombinant vector, $10^7$ virus particles to $10^{11}$ virus particles ($10^5$ IU to $10^9$ IU)/kg in the case of the recombinant virus, and $10^3$ cells/kg to $10^6$ cells/kg in the case of the cell. Specifically, the effective dose of the composition of the present disclosure may be in a range of 0.1 mg/kg to 10 mg/kg in the case of the recombinant vector, $10^8$ particles to $10^{10}$ particles ($10^6$ IU to $10^8$ IU)/kg in the case of the recombinant virus, and $10^2$ cells/kg to $10^5$ cells/kg in the case of the cell. The composition of the present disclosure may be administered one to three times a day. The constituents of the composition of the present disclosure are not necessarily limited thereto, and may vary depending on the condition of a patient and the severity of a disease.

Another embodiment provides a method of inhibiting amyloid-beta aggregation and/or degrading aggregated amyloid-beta, the method including administering, to a subject in need of the inhibition of amyloid-beta aggregation and/or the degradation of aggregated amyloid-beta, a pharmaceutically effective amount of the glycine transporter protein, a fragment thereof or a nucleic acid molecule encoding the protein or the fragment thereof, a vector including the nucleic acid molecule, or a cell transformed with the vector including the nucleic acid molecule, as an active ingredient. The method may further include, prior to the administering, identifying a subject in need of the inhibition of amyloid-beta aggregation and/or the degradation of aggregated amyloid-beta.

Another embodiment provides a method of degrading tau protein (and/or inhibiting the aggregation thereof) and/or inhibiting the phosphorylation of tau protein, the method including administrating, to a subject in need of the degradation of tau protein (and/or inhibition of the aggregation thereof) and/or inhibition of the phosphorylation of tau protein, a pharmaceutically effective amount of the glycine transporter protein, a fragment thereof or a nucleic acid molecule encoding the protein or the fragment thereof, a vector including the nucleic acid molecule, or a cell transformed with the vector including the nucleic acid molecule, as an active ingredient. The method may further include, prior to the administering, identifying a subject in need of the degradation of tau protein (and/or inhibition of the aggregation thereof) and/or inhibition of the phosphorylation of tau protein.

Another aspect provides a method of preventing and/or treating a degenerative brain disease, comprising administering, to a subject in need of the prevention and/or treatment of a degenerative brain disease, a pharmaceutically effective amount of the glycine transporter protein, a fragment thereof or a nucleic acid molecule encoding the protein or the fragment thereof, a vector including the nucleic acid molecule, or a cell transformed with the vector including the nucleic acid molecule, as an active ingredient. The method may further include, prior to the administering, identifying a subject in need of the prevention and/or treatment of a degenerative brain disease.

Another embodiment provides a health functional food for the prevention or amelioration of a degenerative brain disease, including, as an active ingredient, a glycine transporter protein, a fragment thereof or a nucleic acid molecule encoding the protein or the fragment thereof, a vector including the nucleic acid molecule, or a cell transformed with the vector including the nucleic acid molecule, as an active ingredient.

Another embodiment provides a health functional food for the prevention or amelioration of cognitive impairment or enhancing memory, including, as an active ingredient, a glycine transporter protein, a fragment thereof or a nucleic acid molecule encoding the protein or the fragment thereof, a vector including the nucleic acid molecule, or a cell transformed with the vector including the nucleic acid molecule.

The term "cognitive" as used herein may refer to the mental activity or process of gaining knowledge and understanding through thinking, experience, and sensation. In this regard, processes such as knowledge, attention, memory and working memory, judgment and evaluation, reasoning and computation, problem solving and decision-making, and understanding and generation of language may be included. The cognitive impairment belongs to a category of mental health impairments that mainly affect learning, memory, perception, and problem solving, and may include amnesia, dementia, and delirium.

The improvement of memory may refer to improvement of consequences of damage to neuroanatomical structures as well as of storage, retention, and recollection of memories. In addition, the improvement of memory may refer to improvement of memory impairments (including Alzheimer's disease) that can be progressive.

The health functional food may refer to a food prepared using a raw material or ingredient having a nutrient that is easily deficient in daily meals or having a useful function for the human body (hereinafter, referred to as "functional raw material"), and may also refer to any food that helps to maintain health or to prevent and/or ameliorate a certain disease or symptom, and a final product form thereof is not particularly limited. For example, the health functional food may be selected from the group consisting of various foods, beverage compositions, food additives, and the like, but is not limited thereto.

An amount of the active ingredient included in the health functional food appropriately varies depending on the type of food, desired use, or the like and is not particularly limited. For example, the amount may be in a range of 0.0001 wt % to 99 wt %, 0.0001 wt % to 95 wt %, 0.0001 wt % to 90 wt %, 0.0001 wt % to 80 wt %, 0.0001 wt % to 50 wt %, 0.001 wt % to 99 wt %, 0.001 wt % to 95 wt %, 0.001 wt % to 90 wt %, 0.001 wt % to 80 wt %, 0.001 wt % to 50 wt %, 0.01 wt % to 99 wt %, 0.01 wt % to 95 wt %, 0.01 wt % to 90 wt %, 0.01 wt % to 80 wt %, 0.01 wt % to 50 wt %, 0.1 wt % to 99 wt %, 0.1 wt % to 95 wt %, 0.1 wt % to 90 wt %, 0.1 wt % to 80 wt %, 0.1 wt % to 50 wt %, 0.1 wt % to 30 wt %, 0.1 wt % to 10 wt %, 1 wt % to 99 wt %, 1 wt % to 95 wt %, 1 wt % to 90 wt %, 1 wt % to 80 wt %, 1 wt % to 50 wt %, 1 wt % to 30 wt %, 1 wt % to 10 wt %, 10 wt % to 99 wt %, 10 wt % to 95 wt %, 10 wt % to 90 wt %, 10 wt % to 80 wt %, 10 wt % to 50 wt %, 10 wt % to 30 wt %, 25 wt % to 99 wt %, 25 wt % to 95 wt %, 25 wt % to 90 wt %, 25 wt % to 80 wt %, 25 wt % to 50 wt %, 25 wt % to 30 wt %, 40 wt % to 99 wt %, 40 wt % to 95 wt %, 40 wt % to 90 wt %, 40 wt % to 80 wt %, 40 wt % to 50 wt %, 50 wt % to 99 wt %, 50 wt % to 95 wt %, 50 wt % to 90 wt %, 50 wt % to 80 wt %, 60 wt % to 99 wt %, 60 wt % to 95 wt %, 60 wt % to 90 wt %, or 60 wt % to 80 wt %, with respect to the total weight of the food, but is not limited thereto.

The health functional food may further include at least one selected from the group consisting of various nutrients, vitamins, minerals (electrolytes), flavoring agents, such as synthetic or natural flavoring agents, coloring agents, thickeners (cheese, chocolate, and the like), pectic acid or salts thereof, alginic acid or salts thereof, organic acids, protective colloidal thickeners, pH adjusters, stabilizers, preservatives, glycerin, alcohol, carbonation agents used in carbonated beverages, and the like. A ratio of these additive is generally selected from 0.001 parts by weight to about 20 parts by weight with respect to 100 parts by weight of the total health functional food, but is not limited thereto.

The technical terms, methods and the like described for the present disclosure may equally apply to the respective disclosures.

Advantageous Effects of Disclosure

A composition including, as an active ingredient, a glycine transporter protein, a fragment thereof or a nucleic acid molecule encoding the protein or the fragment thereof, a vector including the nucleic acid molecule, or a cell transformed with the vector including the nucleic acid molecule, according to an embodiment, not only can achieve excellent effect(s) of inhibiting amyloid-beta aggregation and/or degrading aggregated amyloid-beta, but also degrades tau protein (and/or inhibition of the aggregation thereof), inhibits the hyperphosphorylation of tau protein, and has excellent blood-brain barrier permeability, thus making it possible to successively act on brain tissues. Therefore, the composition can be effectively applied to the prevention and/or treatment of various degenerative brain diseases associated with amyloid-beta aggregation, tau protein aggregation, and/or hyperphosphorylated tau protein.

BRIEF DESCRIPTION OF DRAWINGS

FIG. 4 illustrates graphs showing the results of confirming the degradation of amyloid-beta plaques in transgenic Alzheimer's dementia animals (APP/PS1 TG) by using thioflavin S staining, showing: the effect of degrading aggregated amyloid-beta via administration of AAV-GlyT1, and a significantly decreased value of the total area of amyloid-beta plaques in the cortex and hippocampus of the brain hemisphere, in a group administered with AAV-GlyT1, as compared to TG mice administered with AAV-GFP as a negative control.

FIG. 5 illustrates the results of carrying out a Y-maze test (Y-shaped maze evaluation) on week 12 after AAV-GlyT1 was administered to transgenic Alzheimer's dementia animals (APP/PS1 TG), the results being values representing spontaneous alteration (%), obtained by measuring the relative frequency at which experimental animals enter the maze sequentially by identifying the surrounding clues, showing that the level of memory is improved close to that of WT-Veh as a positive control, in the experimental groups, as compared to the group administered with AAV-GFP as a negative control.

MODE OF DISCLOSURE

Hereinafter, the present disclosure will be described in further detail with reference to examples. However, these examples are for illustrative purposes only and are not intended to limit the scope of the present disclosure. It is obvious to those of ordinary skill in the art that the examples described below can be modified without departing from the essential teachings of the present disclosure.

Example 1: Confirmation of Decreased GlyT1 Expression in Brain Tissues of Alzheimer's Dementia Patients

1.1. Preparation of Human Brain Tissues

The post-mortem brain tissues of Alzheimer's dementia patients were identified in the frontal lobe and hippocampus of a dementia patient group and a normal control, distributed by the Seoul National University Brain Bank (table 1). Five tissues for an Alzheimer's dementia patient group (AD) and five tissues for a normal control (Non-AD), of which the sex and the age are different, were obtained for experiments.

TABLE 1

| | Block # (region) | Sex | Age |
|---|---|---|---|
| AD | A17-12 | F | 75 |
| | A17-26 | F | 85 |
| | A18-2 | F | 75 |
| | A18-3 | M | 80 |
| | A18-15 | F | 93 |
| Non-AD | A18-10 | M | 56 |
| | A17-17 | M | 74 |
| | A18-17 | M | 75 |
| | A19-3 | M | 78 |
| | A19-7 | M | 71 |
| | A18-11 | F | 74 |

1.2. Immunohistochemical Staining

Fixed brain tissues prepared in Example 1.1. were sectioned to a thickness of 30 μm to perform immunohistochemical staining. The fixed tissues were reacted with a 0.5% thioflavin S solution for 10 minutes to stain Aβ plaques. In addition, tissues were stained using a GlyT1 antibody. After washing twice with 50% ethanol and washing once with DPBS, the stained tissues were mounted on slide glasses and observed with a laser scanning confocal microscope.

Figure 1:
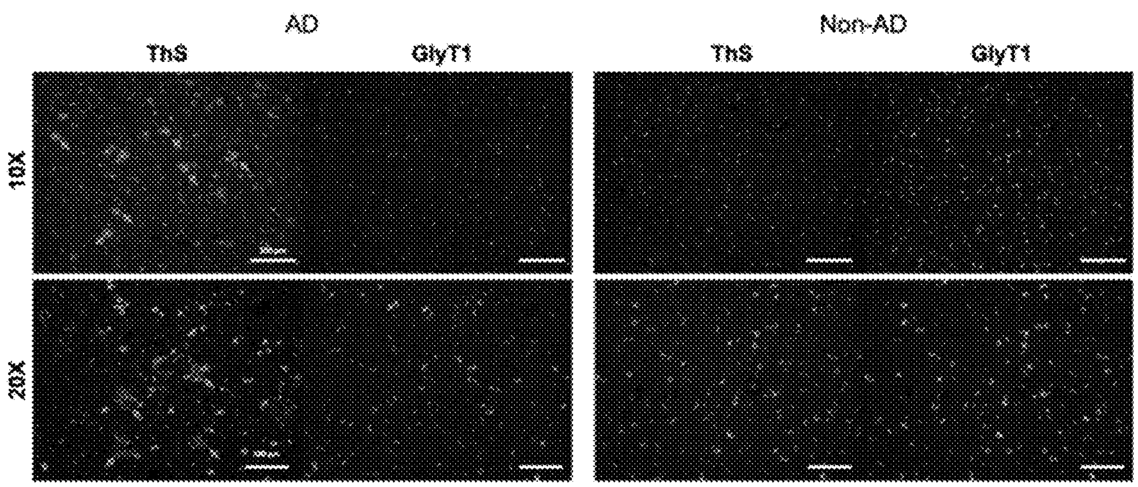
FIG. 1 illustrates tissue staining images showing the results of confirming the expression of GlyT1 in the brain tissues of patients with Alzheimer's dementia, showing that the expression of GlyT1 is significantly low in the brain regions of the patients where plaques are accumulated in the hippocampus and the frontal lobe, compared to a normal control.

As a result of immunohistochemical staining of the brain tissues of normal individuals and Alzheimer's disease patients in FIG. 1, it was confirmed that the expression of GlyT1 was significantly lower than that of a normal control, in the brain regions of the Alzheimer's disease patients where plaques were accumulated in the hippocampus and the frontal lobe.

Example 2: Observation of Pathology of Transgenic Mice by GlyT1 and GlyT2 Inhibition in App/PS1 TG Mice

2.1. Preparation of APP/PS1 TG Mouse Model

Transgenic mice (APP/PS1 TG; Alzheimer's disease animal model; B6C3-Tg (APPswe, PSEN1dE)85Dbo/Mmjax) and wild-type mice were derived from Jackson Laboratory (Bar Harbor, Maine, USA). The APP/PS1 TG mice were crossed with wild-type mice and maintained as double hemizygotes. All genotypes were confirmed through PCR analysis using tail DNA according to the standard PCR conditions of Jackson Laboratory. 1 mouse per plastic cage was accommodated in an animal breeding room, and freely fed food and water under 12 h light/12 h dark cycles while being maintained at 21±1° C.

2.2. Administration of GlyT1 and GlyT2 Inhibitors to Mouse Models

Each of a GlyT1 inhibitor (LY2365109 hydrochloride) and a GlyT2 inhibitor (N-arachidonylglycine) was orally administered daily for 4 weeks at a concentration of 10 mg/kg/day, to 7-month-old transgenic mice in which amyloid-beta plaques had not yet been sufficiently produced.

2.3. Preparation of Brain Tissue Sample

Mice were anesthetized using 2% avertine (20 mg/g, i.p.) The mice were perfused with 0.9% NaCl and the brains thereof were excised. The hemibrains were fixed overnight at 4° C. in 4% paraformaldehyde (pH 7.4).

2.4. Immunohistochemical Staining

The fixed brain tissues prepared in Example 2.3. were sectioned to a thickness of 30 μm to perform immunohistochemical staining. The fixed tissues were reacted with a 0.5% thioflavin S solution for 10 minutes to stain Aβ plaques. After washing twice with 50% ethanol and washing once with DPBS, the stained tissues were mounted on slide glasses and observed with a laser scanning confocal microscope.

Figure 2:
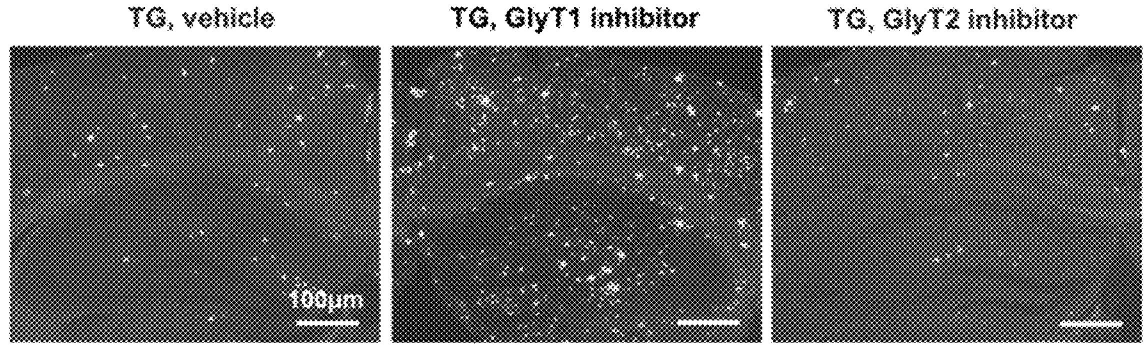
FIG. 2 illustrates tissue staining images showing the results of significantly increased formation of amyloid-beta plaques by the inhibition of GlyT1 in transgenic Alzheimer's dementia animals (APP/PS1 TG) in which amyloid-beta plaques have not yet been sufficiently formed, in which an increase in plaques by the inhibition of GlyT2 as a control was not observed, indicating that GlyT1 is specifically involved in the formation of amyloid-beta plaques.

As a result, as illustrated in the staining images of amyloid-beta plaques of FIG. 2, it was confirmed that, compared to the mice (TG GlyT2 inhibitor) administered with the GlyT2 inhibitor, the number and the total area of the plaques were significantly increased in the mice administered with the GlyT1 inhibitor (TG, GlyT1 inhibitor). This indicates that GlyT1 is specifically involved in the formation of amyloid-beta plaques.

Example 3: Confirmation of Effect of AAV-GlyT1 Administered into Cisterna Magna on Reducing Amyloid Plaques in APP/PS1 TG Mice 3.1. Preparation of APP/PS1 TG Mouse Model Transgenic mice (APP/PS1 TG; Alzheimer's disease animal model; B6C3-Tg (APPswe, PSEN1dE)85Dbo/Mmjax) and wild-type mice were derived from Jackson Laboratory (Bar Harbor, Maine, USA). The APP/PS1 TG mice were crossed with wild-type mice and maintained as double hemizygotes. All genotypes were confirmed through PCR analysis using tail DNA according to the standard PCR conditions of Jackson Laboratory. 1 mouse per plastic cage was accommodated in an animal breeding room, and freely fed food and water under 12 h light/12 h dark cycles while being maintained at 21±1° C.

3.2. Adeno-Associated Virus (AAV)-GlyT1 Administration to Mouse Model

AAV (AAV-GlyT1) expressing the glycine transporter (GlyT1) of SEQ ID NO: 1 was recombined according to the production method of Vigene Biosciences (Rockville, MD, USA).

Specifically, an expression vector was constructed by inserting the GlyT1 gene into AAV having an AAV9 serotype, and then the vector was transduced into packaging cells, the transduced packaging cells were cultured and then filtered to obtain a solution including AAV particles, which was then concentrated and purified. Thereafter, AAV-GlyT1 was administered once to the cisterna magna of 5-month-old APP/PS1 TG mice at a concentration of $5\times10^{10}$ viral particles (VPs) or $1.5\times10^{11}$ VPs. $5\times10^{10}$ VPs of AAV-GFP was administered to a control.

3.3. Preparation of Brain Tissue Sample

Mice were anesthetized using 2% avertine (20 mg/g, i.p.) The mice were perfused with 0.9% NaCl and the brains thereof were excised. The hemibrains were fixed overnight at 4° C. in 4% paraformaldehyde (pH 7.4).

3.4. Immunohistochemical Staining

The fixed brain tissues prepared in Example 1.3. were sectioned to a thickness of 30 μm to perform immunohistochemical staining. The fixed tissues were reacted with a 0.5% thioflavin S solution for 10 minutes to stain Aβ plaques. After washing twice with 50% ethanol and washing once with DPBS, the stained tissues were mounted on slide glasses and observed with a laser scanning confocal microscope.

Figure 3:
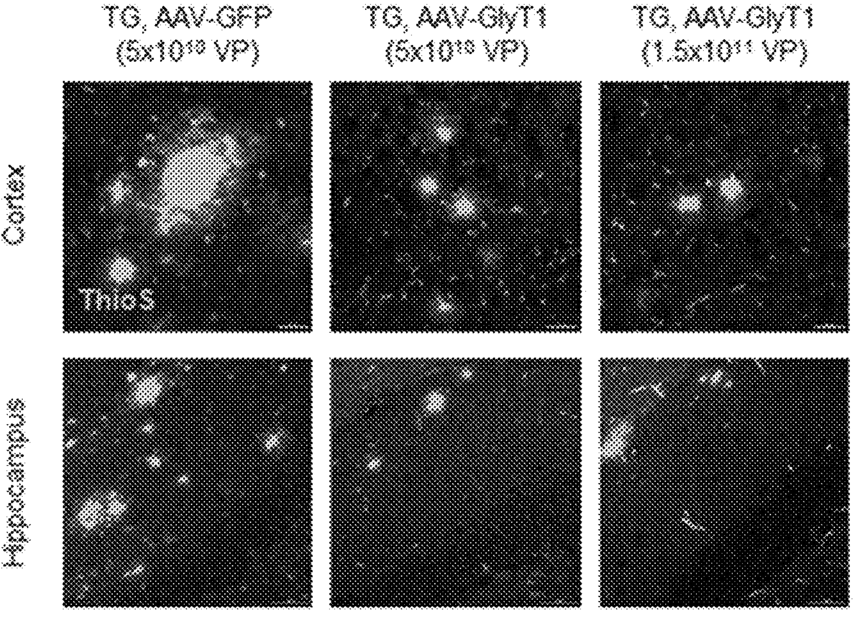
FIG. 3 illustrates tissue staining images showing the results of confirming the degradation of amyloid-beta plaques in transgenic Alzheimer's dementia animals (APP/PS1 TG) by using thioflavin S staining, showing the effect of degrading aggregated amyloid-beta via administration of AAV-GlyT1.

As a result, as illustrated in the staining images of amyloid-beta plaques of FIG. 3 and the graphs of FIG. 4, it was confirmed that, compared to the mice as a control (TG-Veh), the number and the total area of the plaques were significantly decreased in the mice administered with AAV-GlyT1.

Example 4: Confirmation of Effect of AAV-GlyT1 Administered into Cisterna Magna on Improving Cognitive Function in APP/PS1 TG Mice 4.1. Preparation of APP/PS1 TG Mouse Model Transgenic mice (APP/PS1 TG; Alzheimer's disease animal model; B6C3-Tg (APPswe, PSEN1dE)85Dbo/Mmjax) and wild-type mice were derived from Jackson Laboratory (Bar Harbor, Maine, USA). The APP/PS1 TG mice were crossed with wild-type mice and maintained as double hemizygotes. All genotypes were confirmed through PCR analysis using tail DNA according to the standard PCR conditions of Jackson Laboratory. 1 mouse per plastic cage was accommodated in an animal breeding room, and freely fed food and water under 12 h light/12 h dark cycles while being maintained at 21±1° C.

4.2. Administration of AAV-GlyT1 to Mouse Model

AAV-GlyT1 produced using the same method as that used in 1.2 above was administered once to the cisterna magna of 5-month-old APP/PS1 TG mice at a concentration of $5\times10^{10}$ viral particles (VPs) or $1.5\times10^{11}$ VPs. $5\times10^{10}$ VPs of AAV-GFP was administered to a control.

4.3. Y-Maze Test (Y-Shaped Maze Evaluation)

Y-maze test was performed using a maze structure made by placing the same three arms having a length of 40 cm (15 cm in height of the wall) at an angle of 120 degrees. This experiment is a behavioral experiment using the instinctive search habits of rodents, and is a method based on the high possibility of exploring new areas. The more the test animal remembered the last arm it searched for and did not enter the same arm, the higher the memory was. The search time was 8 minutes per subject, and the final result was expressed as a spontaneous alteration (%) value.

Spontaneous alteration (%) was calculated using the following expression.

[Expression]Spontaneous alteration (%)=The number of triplet/(total arm entry-2)

Behavioral patterns were analyzed using SMART VIDEO TRACKING Software (Panlab, USA). All data obtained in the experiments were expressed as mean±standard error mean (SEM), and the drug-applied group was compared with a group to which the drug was not applied, to perform between-group analysis with a student's t-test.

As illustrated in FIG. 5, as a result of performing the Y-maze test on week 12 after AAV-GlyT1 was administered to transgenic Alzheimer's dementia animals (APP/PS1 TG), it was confirmed that the spontaneous alteration (%) value, obtained by measuring the relative frequency of entering the maze sequentially by identifying the surrounding clues, was increased closer to a positive control (WT, Veh) compared to a negative control (TG, AAV-GFP).

The invention claimed is:

1. A method of preventing, ameliorating or treating amyloid-beta aggregation-caused degenerative brain disease, the method comprising administering to a subject in need thereof a therapeutically effective amount of a vector comprising a nucleic acid molecule encoding a glycine transporter protein, wherein the glycine transporter protein is glycine transporter-1 (GlyT1), wherein the subject has a higher level or a higher risk of aggregation of amyloid-beta than normal individuals not having a degenerative brain disease, and wherein the amyloid-beta aggregation-caused degenerative brain disease is selected from the group consisting of Alzheimer's disease, Parkinson's disease, Huntington's disease, mild cognitive impairment, cerebral amyloid angiopathy, amyloid stroke, senile dementia, and amyotrophic lateral sclerosis.

2. The method of claim 1, wherein the vector is any one selected from the group consisting of a plasmid vector, a cosmid vector, a bacteriophage vector, an adenoviral vector, a retroviral vector, and an adeno-associated viral vector.

3. The method of claim 2, wherein the adeno-associated viral vector is any one selected from the group consisting of AAV1, AAV2, AAV3, AAV4, AAV5, AAV6, AAV7, AAV8, AAV9, AAV10, and AAV11.

4. The method of claim 1, wherein the GlyT1 comprises an amino acid sequence encoded by a polynucleotide sequence of SEQ ID NO: 1.

5. The method of claim 1, wherein the aggregation of the amyloid-beta is caused by glycine.

* * * * *

SEQUENCE LISTING

```
Sequence total quantity: 1
SEQ ID NO: 1             moltype = DNA  length = 1956
FEATURE                  Location/Qualifiers
source                   1..1956
```

-continued

```
                        mol_type = genomic DNA
                        organism = Homo sapiens
SEQUENCE: 1
atgagcggcg gagacacgcg ggctgcgatc gctcgcccca ggatggccgc ggctcatgga  60
cctgtggccc cctcttcccc agaacagaat ggtgctgtgc ccagcgaggc caccaagagg  120
gaccagaacc tcaaacgggg caactggggc aaccagatcg agtttgtact gacgagcgtg  180
ggctatgccg tgggcctggg caatgtctgg cgcttcccat acctctgcta tcgcaacggg  240
ggaggcgcct tcatgttccc ctacttcatc atgctcatct tctgcgggat ccccctcttc  300
ttcatggagc tctccttcgg ccagtttgca agccaggggt gcctgggggt ctggaggatc  360
agccccatgt tcaaaggagt gggctatggt atgatggtgg tgtccaccta catcggcatc  420
tactacaatg tggtcatctg catcgccttc tactacttct tctcgtccat gacgcacgtg  480
ctgccctggg cctactgcaa taacccctgg aacacgcatg actgcgccgg tgtactggac  540
gcctccaacc tcaccaatgg ctctcggcca gccgccttgc ccagcaacct ctcccacctg  600
ctcaaccaca gcctccagag gaccagcccc agcgaggagt actggaggct gtacgtgctg  660
aagctgtcag atgacattgg gaactttggg gaggtgcggc tgcccctcct tggctgcctc  720
ggtgtctcct ggttggtcgt cttcctctgc ctcatccgag ggtcaagtc ttcagggaaa  780
gtggtgtact tcacggccac gttcccctac gtggtgctga ccattctgtt tgtccgcgga  840
gtgaccctgg agggagcctt tgacggcatc atgtactacc taaccccgca gtgggacaag  900
atcctggagg ccaaggtgtg ggtgatgct gcctcccaga tcttctactc actgggctgc  960
gcgtggggag gcctcatcac catggcttcc tacaacaagt tccacaataa ctgttaccgg  1020
gacagtgtca tcatcagcat caccaactgt gccaccagcg tctatgctgg cttcgtcatc  1080
ttctccatcc tcggcttcat ggccaatcac ctgggcgtgg atgtgtcccg tgtggcagac  1140
cacggccctg gcctggcctt cgtggcttac cccgaggccc tcacactact tcccatctcc  1200
ccgctgtggt ctctgctctt cttcttcatg cttatcctgc tggggctggg cactcagttc  1260
tgcctcctgg agacgctggt cacagccatt gtggatgagg tggggaatga gtggatcctg  1320
cagaaaaaga cctatgtgac cttgggcgtg gctgtggctg gcttcctgct gggcatcccc  1380
ctcaccagcc aggcaggcat ctattggctg ctgctgatgg acaactatgc ggccagcttc  1440
tccttggtgg tcatctcctg catcatgtgt gtggccatca tgtacatcta cgggcaccgg  1500
aactacttcc aggacatcca gatgatgctg ggattcccac caccctctt ctttcagatc  1560
tgctggcgct tcgtctctcc cgccatcatc ttctttattc tagttttcac tgtgatccag  1620
taccagccga tcacctacaa ccactaccag tacccaggct gggccgtggc cattggcttc  1680
ctcatggctc tgtcctccgt cctctgcatc cccctctacg ccatgttccg gctctgccgc  1740
acagacgggg acaccctcct ccagcgtttg aaaaatgcca caaagccaag cagagactgg  1800
ggccctgccc tcctggagca ccggacaggg cgctacgccc ccaccatagc cccctctcct  1860
gaggacggct tcgaggtcca gccactgcac ccggacaagg cgcagatccc cattgtgggc  1920
agtaatggct ccagccgcct ccaggactcc cggata                            1956
```